(12) United States Patent
Collazo

(10) Patent No.: US 7,618,420 B2
(45) Date of Patent: Nov. 17, 2009

(54) LOCKING INTRAMEDULLARY JIG

(75) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 472 days.

(21) Appl. No.: 11/060,154

(22) Filed: Feb. 17, 2005

(65) Prior Publication Data

US 2006/0184173 A1    Aug. 17, 2006

(51) Int. Cl.
   *A61F 5/00* (2006.01)
(52) U.S. Cl. ...................... 606/87; 606/86 R
(58) Field of Classification Search ............ 606/62–64, 606/86–89, 96–98, 86 R
   See application file for complete search history.

(56) References Cited

U.S. PATENT DOCUMENTS

| | | | |
|---|---|---|---|
| 4,530,263 A | | 7/1985 | Muntel |
| 4,658,875 A | | 4/1987 | Grabovac |
| 4,952,213 A | * | 8/1990 | Bowman et al. ............ 606/79 |
| 5,304,181 A | * | 4/1994 | Caspari et al. ............ 606/80 |
| 5,354,300 A | * | 10/1994 | Goble et al. ............ 606/80 |
| 5,445,640 A | * | 8/1995 | Johnson et al. ........... 606/86 |
| 5,628,749 A | * | 5/1997 | Vendrely et al. .......... 606/80 |
| 5,628,750 A | * | 5/1997 | Whitlock et al. .......... 606/88 |
| 5,681,316 A | * | 10/1997 | DeOrio et al. ............ 606/88 |
| 5,688,280 A | | 11/1997 | Booth, Jr. et al. |
| 5,817,097 A | | 10/1998 | Howard et al. |
| 5,911,723 A | * | 6/1999 | Ashby et al. ............ 606/88 |
| 6,267,762 B1 | | 7/2001 | Millard et al. |
| 2004/0122441 A1 | * | 6/2004 | Muratsu .................. 606/102 |

OTHER PUBLICATIONS

Duracon® and Scorpio® Total Knee Systems Surgical Protocol, Xcelerate Instrumentation, pp. 25-28, Stryker Howmedica Osteonics Catalog, 2000, 2001.

* cited by examiner

*Primary Examiner*—Thomas C Barrett
*Assistant Examiner*—James L. Swiger
(74) *Attorney, Agent, or Firm*—Lerner, David, Littenberg, Krumholz & Mentlik, LLP

(57) ABSTRACT

A locking intramedullary alignment jig for use in bone resection, especially for the proximal tibial has an axially extending intramedullary rod for insertion into the medullary canal of the tibia. A slidable anchoring block is mounted on the rod for movement along the rod in the axial direction, which on the tibia is the proximal-distal direction. The anchoring block has a pivot point at one end thereof and a tooth portion at a second end thereof. A first rotating body is pivotally coupled to the pivot point on the anchoring block for rotation about a first axis. The rotating body includes a toothed locking member for releasable locking engagement with the toothed portion the anchoring block. A second rotating body, including a bone resection guide is connected to the first rotating body. Movement of the first and second rotating bodies allow rotation of the resection guide in both the flexion-extension and varus-valgus directions.

23 Claims, 7 Drawing Sheets

LOCKING INTRAMEDULLARY JIG

BACKGROUND OF THE INVENTION

This invention relates to an alignment jig used to place and align a cutting guide in order to make a transverse cut on the tibia and/or femur.

Intramedullary instruments are used by surgeons to place and subsequently align a cutting guide on a tibia or femur to a specific flexion-extension and varus-valgus angle with respect to the mechanical axis of the tibia or femur. Once the cutting guide is aligned to the desired settings, it is pinned to the bone for stability and used to guide a saw blade to make a transverse cut on the bone as required in total knee replacement surgery. The transverse cut would be on the proximal tibia or distal femur.

A drawback of some of these instruments is that once varus-valgus and flexion-extension adjustments are made and locked in place, this alignment setting can slip during the subsequent pinning of the cutting guide to the proximal tibia.

Typically, the alignment settings are locked by tightening a thumbscrew. The holding power of the screw is proportional to the amount of torque that is applied to the thread by the surgeon. Slippage may occur because the amount of torque that can be applied by hand to a knob of limited size, and with slippery gloves is somewhat limited. Additionally, if the jig remains in place during the cutting operation, as is usual in revision surgery, the vibration caused by the saw may loosen the screws.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

SUMMARY OF THE INVENTION

It is one aspect of the invention to provide a bone cutting instrument having a quick, easy and ergonomic adjustment by simply depressing a button, and a positive non-slip locking by releasing the button.

It is a further aspect of the invention to provide an instrument having tactile and audible feedback that lets surgeons know how many degrees rotation have been adjusted.

There are significant advantages with this device over the prior art devices. The instrument of the present invention provides a non-slipping locking mechanism that does not rely on a threaded thumbscrew.

Another advantage of the present invention is that that a surgeon can detect through tactile feedback the precise amount of flexion-extension or anterior-posterior degrees that has been adjusted without relying on visual scribed lines. As a result of a spring-loaded shuttle, each degree being adjusted results in a detectable change in the force that is applied to rotate the jig. Once an adjustment is made, the jig will remain at this setting upon the release of the locking button, making the adjustment and locking function very easy for the user. A spring loaded wedge-like toothed shuttle is used to lockingly engage a ratchet on angle adjustor when the button is released. When the release button is pushed in then the shuttle teeth can ride over the teeth of ratchet. An added benefit of the spring-loaded shuttle is that with each degree of adjustment, an audible click is produced, thereby allowing the surgeon to make precise adjustments based on audible feedback.

These and other advantages of the present invention are provided by a locking intramedullary jig for use in bone resection surgery which jig mounts on an axially extending intramedullary rod, a trial stem, or intramedullary reamer for insertion into the medullary canal of a long bone such as a tibia or femur. The jig includes a slide block mounted on the intramedullary rod for movement along the rod in an axial direction. On the femur or tibia this is the proximal-distal direction. The slide block has a pivot point at one end thereof and a toothed portion and a second end thereof. A first rotating body is pivotally coupled to the pivot point on the slide block for rotation about a first axis generally perpendicular to the axis of the rod. The rotating body includes a toothed locking member or pawl moveably mounted thereon for releasable locking engagement with the toothed portion on the slide block. A bone resection guide is coupled to the first rotating body either directly or indirectly via a second rotating body.

The first rotating body of the jig includes a spring biased shaft mounted thereon with a first end engagable with the toothed locking member or pawl for moving the toothed locking member relative to the first rotating body into locking engagement with the toothed portion on the slide block. The spring biased shaft is moveable against the spring to a position which allows movement of the teeth on the toothed locking member away from the teeth on the slide block toothed portion to permit relative movement therebetween. This movement of the teeth away from one another can be limited so as to allow the teeth to slide up and over one another as the angle between the slide block and first rotating body about the pivot point changes. This produces the tactile and audible feedback.

Preferably, the jig has a second body with a rotating body part rotatably coupled to the first rotating body and a non-rotatable part fixed with respect to the first rotating body. The rotating part of the second body has a bone resection guide mounted thereon. The second body has a non-rotatable tooth portion mounted on the non-rotatable part and a rotatable portion coupled to the bone resection guide. The rotatable portion of the second body has a moveable locking pawl with the toothed portion for releasable locking engagement with a non-rotatable toothed portion of the second body. The rotating part of the second body includes a spring biased shaft mounted thereon with a first end engagable with the toothed locking pawl on the rotatable part. The shaft is spring biased for moving the toothed locking pawl into engagement with the non-rotatable toothed portion thereon. The spring biased shaft including the locking pawl is moveable against the spring to a position which allows movement of the teeth of the locking pawl away from the teeth on the non-rotatable toothed portion of the second body in a manner similar to that described above with regard to the first rotating body.

When used in connection with the femur or tibia, the cutting jig is mounted on an intramedullary rod (IM) which extends along the mechanical axis of either the tibia or femur which axis extends in a generally proximal-distal direction. Thus, the first rotating body rotatably coupled to the slide block mounted on the IM rod, trial stem, or reamer rotates about a medial-lateral axis. The rotating part of the second body portion then rotates about a generally anterior-posterior axis. Thus, the movement of the first body portion with respect to the slide block sets the flexion extension angle of the proximal tibia or distal femur and the rotating part of the second body sets the varus-valgus angle of the proximal cut on the tibia or the distal cut on the femur.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 1:
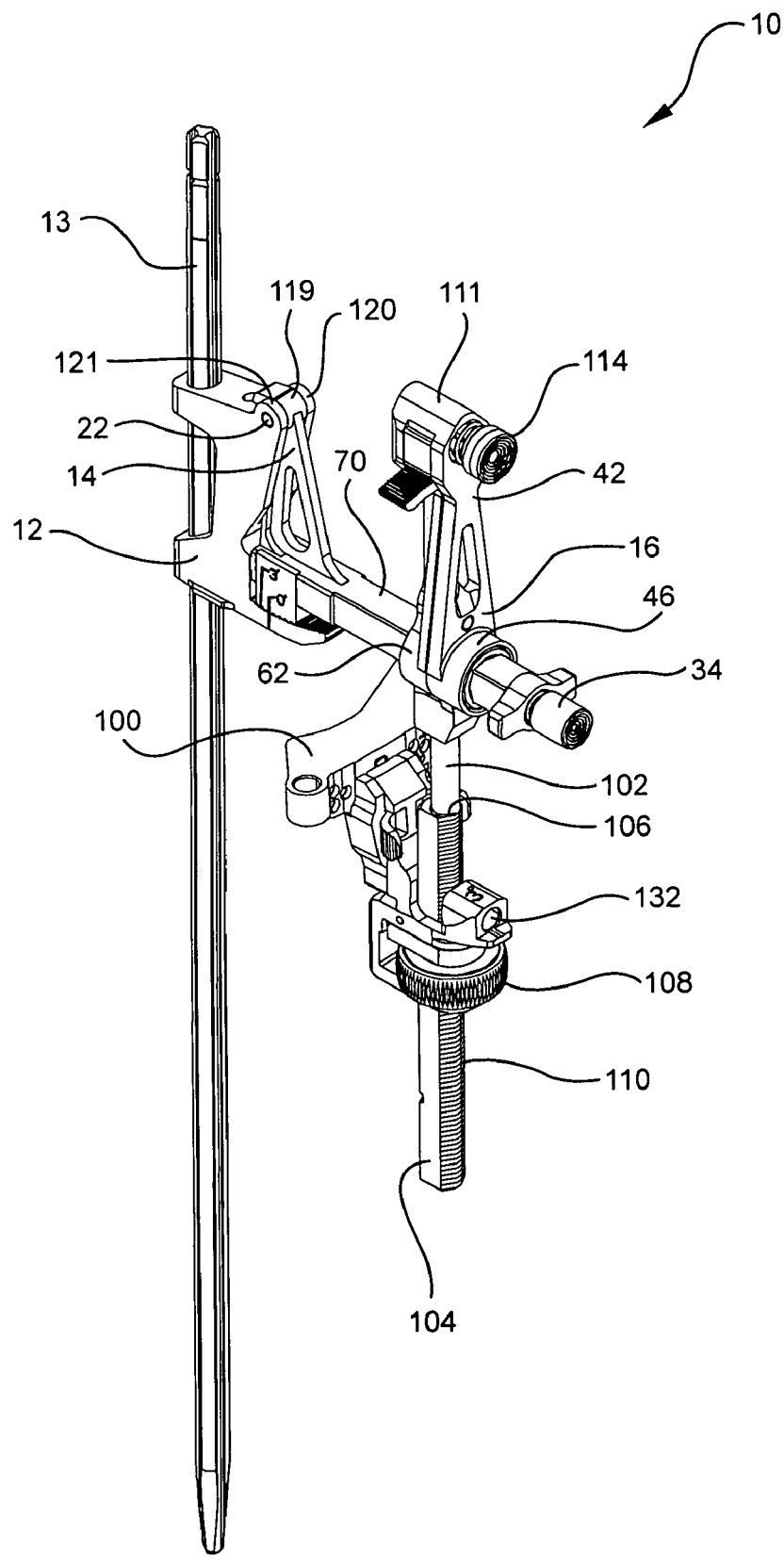
FIG. 1 is an isometric view of the locking intramedullary tibial jig of the present invention mounted on a intramedullary rod capable of being mounted in the canal of a long bone such as the tibia.
Figure 2:
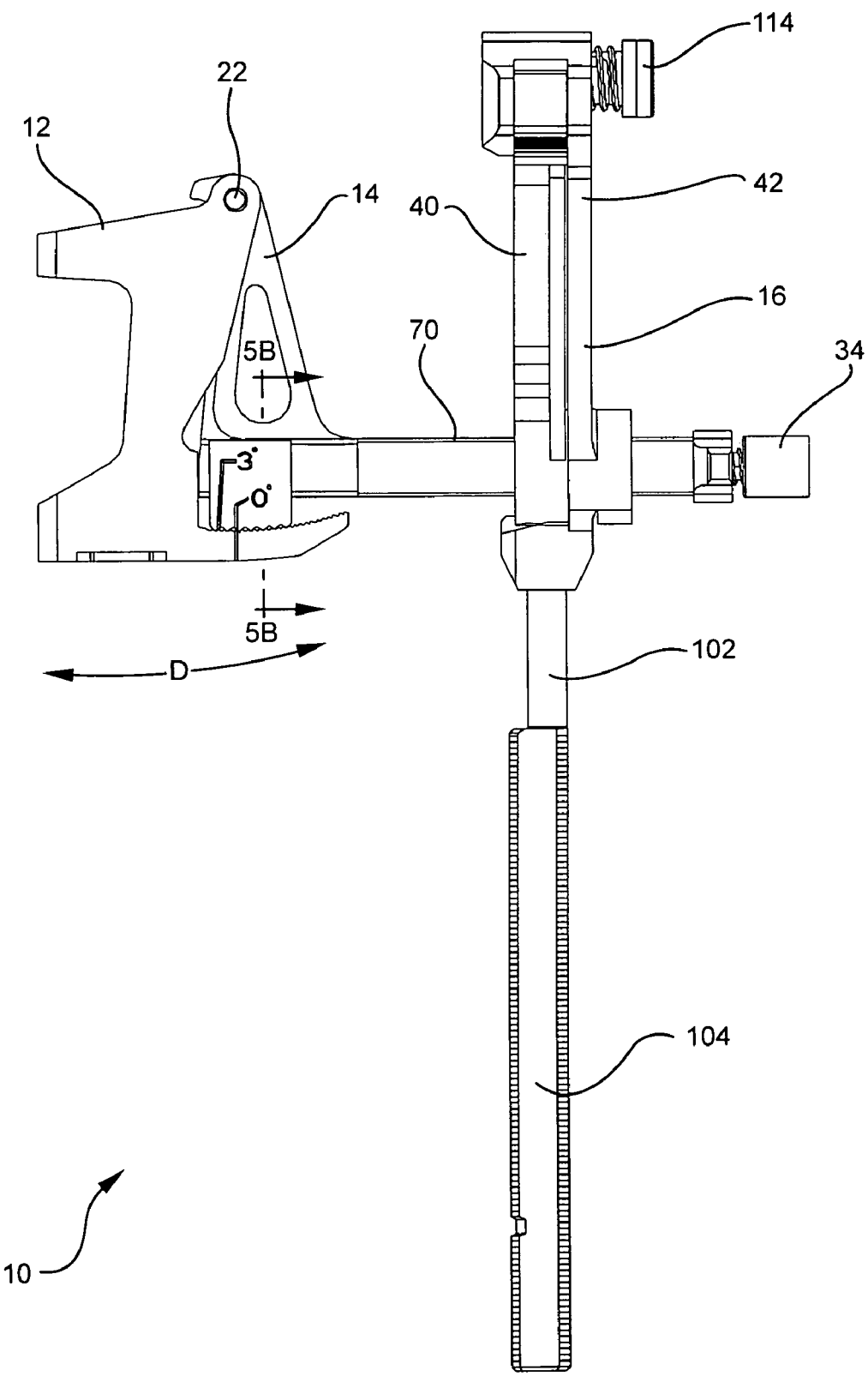
FIG. 2 is a side elevation view of the locking intramedullary tibial jig of FIG. 1.
Figure 3:
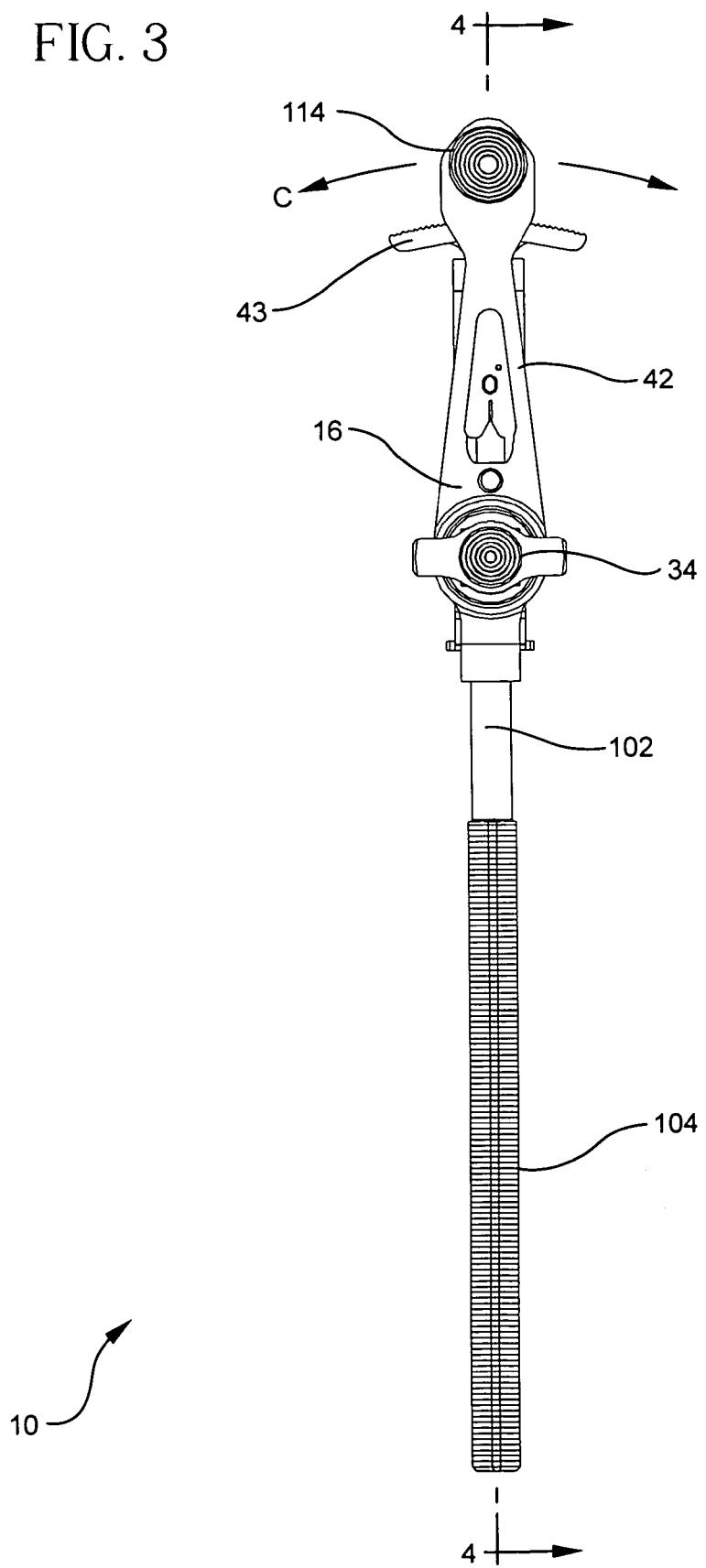
FIG. 3 is an end view of the locking intramedullary jig from the right hand side of FIG. 2.

Referring to FIGS. 1 to 4 there is shown the tibial jig of the present invention generally denoted as 10. Jig 10 consists of an assembly containing three main functional elements: a main anchoring block 12, which connects to an IM rod 13 via bore 18 for sliding movement therealong. A first rotatable body or arm 14 is pivotally coupled to block 12 to adjust flexion-extension settings and a second body or arm 16 which includes a rotating part 42. Rotatable part 42 is coupled to slide block 12 via body 14 to adjust varus-valgus settings. Body 16 may be connected, either directly or indirectly via body part 14 to slide block 12. IM rod 13 is inserted into the medullary canal of a long bone such as the tibia (not shown) in a standard manner.

Cutting jig 10 further includes a cutting guide block 100 mounted thereon for vertical, i.e. proximal-distal movement with respect to a rod 104 mounted on body part 16. Block 100 is slidably adjusted along the length of a rod 104 and can be locked at a desired location therealong. Preferably, block 100 is detachable from jig 10 so that the entire jig 10 can be removed after block 100 is pinned to the bone. Rod 104 forms part of the rotating part structure 42 which sets the varus-valgus angular adjustment.

In the preferred embodiment, rod 104 is, at least partially, threaded and is fixedly attached to a non-threaded rod 102. Rod 104 may have a bore 106 adapted to receive rod 102. Rod 104 can be fixedly attached to rod 102 by, for example, preferably welding or using a threaded coupling device (not shown) which can be used for selectively locking rod 102 in the bore of rod 104. Rod 102 is preferably welded to the main bushing body. Preferably gross vertical (proximal-distal) adjustment of the cutting block can be made either by sliding rod 102 in the bore 106 of rod 104 in the proximal-distal direction or if rods 104, 106 are threadably coupled by rotating the rods about the aligned axes of rods 102, 104, or by using the adjustment system described in co-pending U.S. application Ser. No. 10/782,615 the teachings of which are incorporated herein by reference. After the gross adjustment is made, rods 102 and 104 are rigidly coupled together by the coupling device and fine proximal-distal adjustment can be made by rotating a wheel 108 which has a threaded internal bore adapted to engage external threads 110 on rod 104. This can be done by having the threads rotatably engage each other or radially engage each other in a rachet-like manner so that they can move radially into and out of engagement. Thus, movement of wheel 108 provides a fine adjustment of cutting guide 100 in the proximal-distal direction. This adjustment can be made before or after the flexion-extension angle is set utilizing rotatable body or arm 14 and either before or after setting the varus-valgus angle with second arm 16. Preferably this adjustment is made after both angles are set. Alternately, rotation or release of wheel 108 can provide the sole adjustment of block 100 along threaded rod 104.

Figure 4:
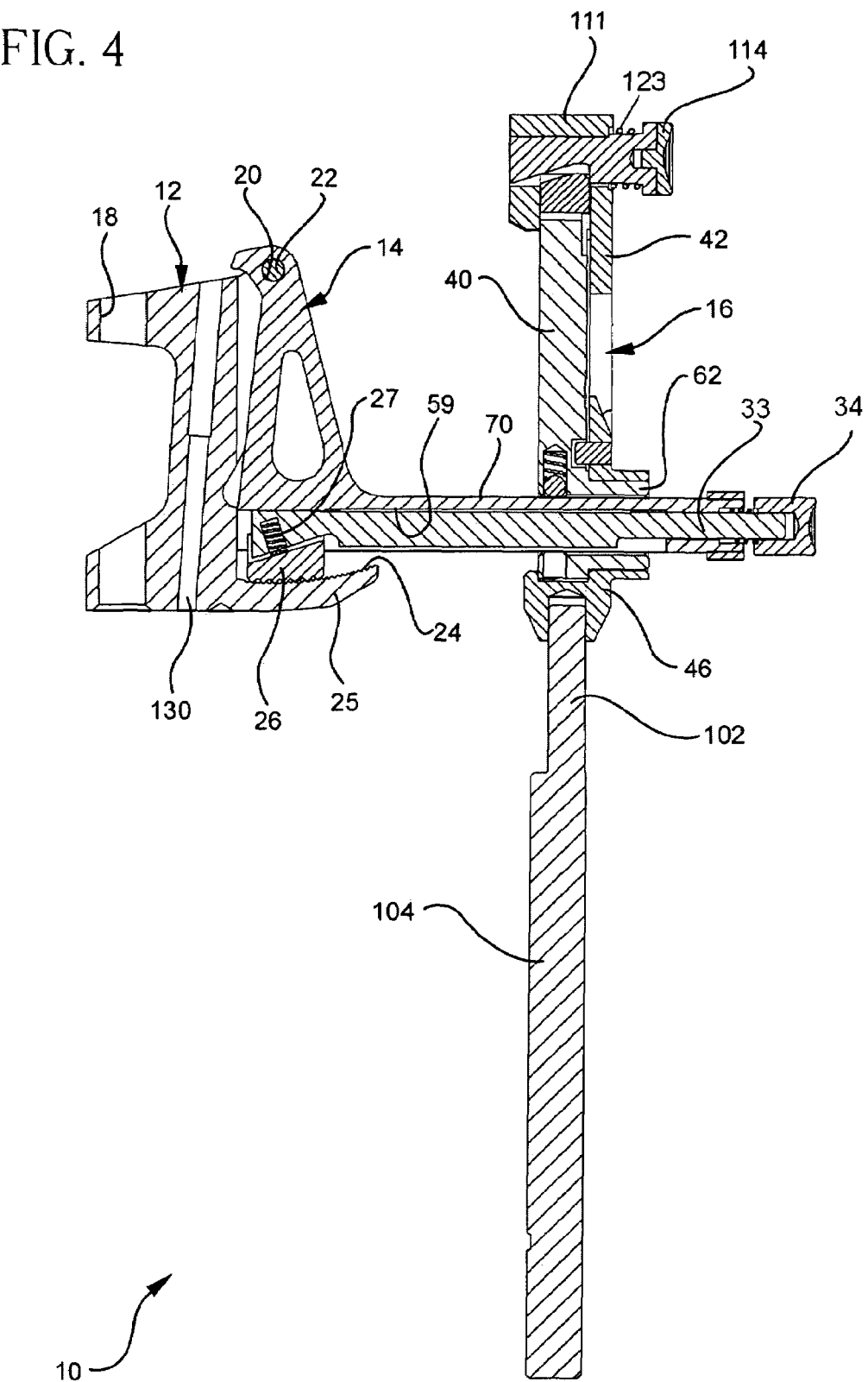
FIG. 4 is a cross-sectional view along lines 4-4 of FIG. 3.
Figure 5:
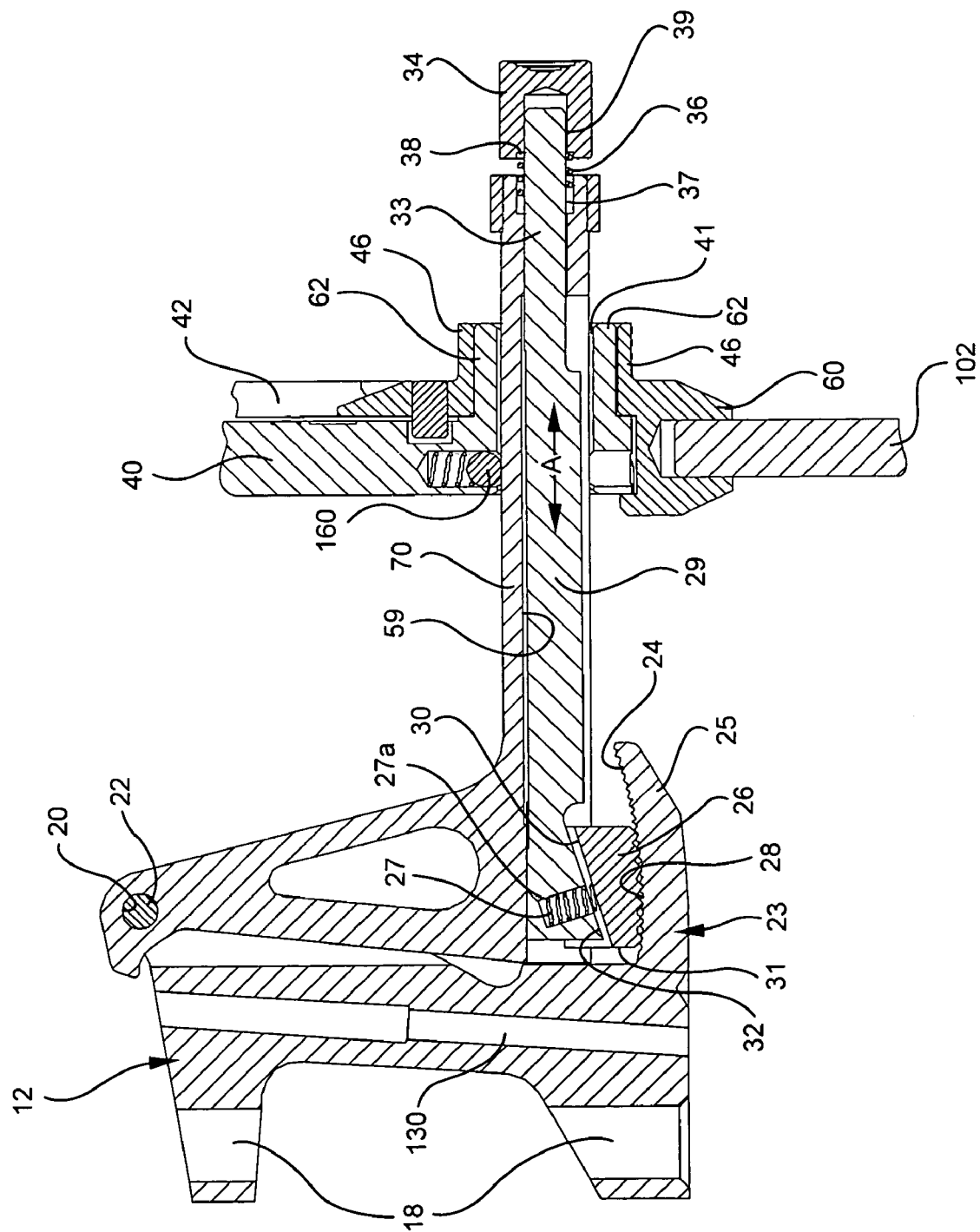
FIG. 5 is an enlarged view of the flexion-extension adjustor of FIG. 4.

Referring to FIGS. 1, 4, and 5, the preferred main anchoring or slide block 12 is shown. Block 12 is used to mount tibial jig 10 on the proximal tibia (not shown) via the rod 13. Block 12 contains an aperture 18 that accepts IM rod 13 which rod has been previously driven into the intramedullary canal of the tibia. Block 12 normally is free sliding and bottoms on the tibia. Alternatively, block 12 may include a releasable locking system which fixes block 12 to the rod 13. In the preferred embodiment, rotatable arm 14 has a flange or bushing 119 rotatably coupled to anchoring block 12 between a pair of forks 120 and 121 thereon each having aligned matching holes 20, which are cross-pinned with a hinge pin 22 to form a hinged joint with flange 119. Anchoring block 12 also has a lower curved tooth portion 23 having teeth 24 formed on curved flange 25 concentrically arranged about the axis of hole 20. In the preferred embodiment, tooth pattern 24 is made with teeth spaced in increments of 1 degree about center of pin 22.

In the preferred embodiment, a moveable locking pawl or shuttle 26 is attached to a lower end of first rotating arm 14 within a recessed guide track 130 that allows movement of the shuttle or locking pawl 26 only in a direction towards or away from teeth 24 of block 12. The outwardly facing surface of shuttle 26 contains a curved tooth pattern 28 which can engage with the curved tooth pattern 24 on the anchoring block 12. Shuttle 26 is spring biased, preferably by a coil spring 27a, in a direction that maintains the mating tooth patterns 24 and 28 in constant engagement. Shuttle or pawl 26 contains a ramp 30 that engages with a mating ramp 32 on one end of an actuating shaft 29. Actuating shaft 29 is mounted within a hollow shaft portion 70 integral with arm 14.

Figure 5A:
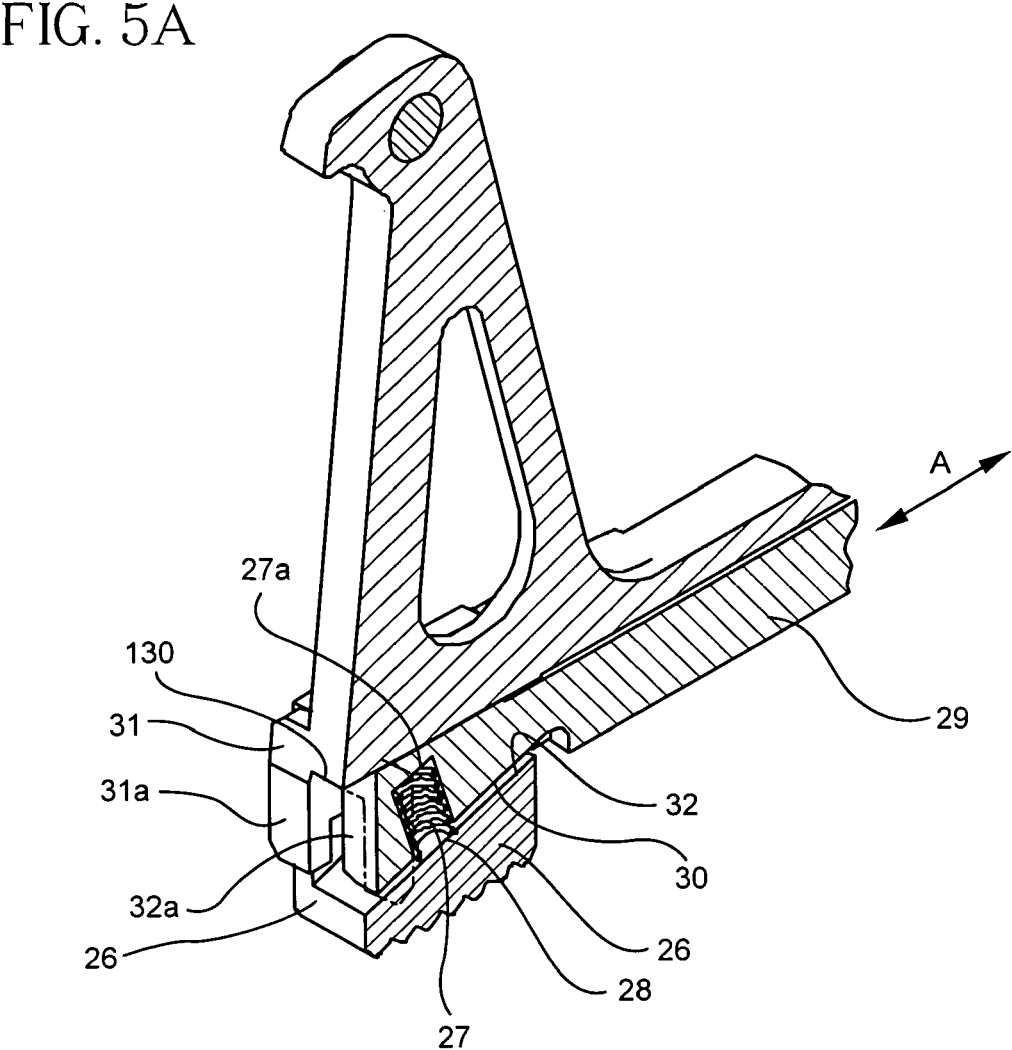
FIG. 5A is an end view in perspective of the actuating shaft and locking shuttle shown in FIG. 5.
Figure 5B:
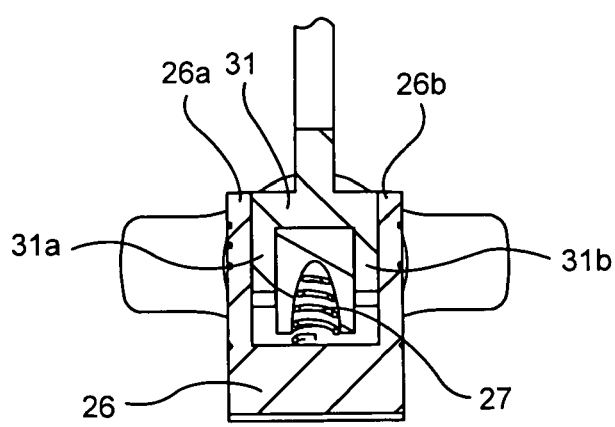
FIG. 5B is a cross-sectional view of the locking shuttle shown in FIG. 2 along lines 5B-5B.

Referring to FIGS. 5, 5A and 5B in the preferred embodiment hollow shaft portion 70 includes a bore 59 for receiving an actuating shaft 29. The outer shape of shaft 29 and the bore 59 is preferably square to prevent the relative rotation of these parts. Of course, other shapes could be used as long as rotation of shaft 29 within bore 59 is prevented. In the preferred embodiment, actuating shaft 29 has a leading end 31 with an open bore 27. A coil spring 27a is mounted in bore 27 at first end 31. In the preferred embodiment, as shown in FIG. 5a, locking pawl 26 is bifurcated at 26a and 26b to form track 130 which receives a tongue 31a of end 31. Parts 26a and 26b of pawl 26 extend from a lower form a portion of shuttle or locking pawl 26. Tongue 31a slides back and forth in Direction "A" in track 130 formed between the bifurcated arms 26a, 26b of pawl 26 as shaft 29 is actuated. As stated above, shuttle 26 moves in a direction toward and away from teeth 24 as shaft 29 is moved within bore 59. Shaft 29 has a second end 33 with a button 34 coupled thereto. A coil spring 36 is located between end 33 of shaft 29 and engages a boss 38 surrounding a bore 39 in button 34. In the preferred embodiment coil spring 36 sits in a recessed bore 37 in hollow shaft 70 and surrounds a reduced section at end 33 of actuating shaft 29.

Shaft 29 is slidably mounted within hollow shaft portion 70 of rotating arm 14 and is spring biased by spring 36 in the direction that maintains both mating ramps 30 and 32 in constant engagement, i.e. towards the right in FIG. 5.

Thus, in its biased state, ramp 32 of actuating shaft 29 forces the shuttle 26 in the direction that rigidly locks the mating tooth patterns 24 and 28. Since actuating shaft 29 is spring loaded in the locked direction, the ramps 30 and 32 engage and force shuttle 26 into engagement with teeth 24 thus prohibiting the shuttle 26 from moving sufficiently to disengage the teeth 24 and 28. This locked position makes it impossible for the mechanism to inadvertently slip from the locked to the released position. Conversely, when actuating shaft 29 is moved forward (to the left of FIG. 5) by depressing button 34 ramps 30 and 32 are moved out of engagement such that a clearance is formed between them. On movement of block 12 with respect to arm 14 about pivot point at the holes 20, this clearance permits tooth pattern 28 on shuttle or pawl 26 to compress spring 27a as it rides over the crests of teeth 24 on flange 25. This occurs because shuttle 26 is not free floating but rather, spring biased by spring 27a in the direction that maintains the tooth patterns 24 and 28 in constant engagement. However, spring 27a is sized to permit its compression by shuttle 26 upon the manual rotational movement of block 12 with respect to arm 14 about pivot point at holes 20. A perceptible increase and decrease in resistance is felt by the user as each tooth is engaged and disengaged during the adjustment process. In addition to the tactile feedback an audible clicking can be heard by the user.

Referring to FIGS. 3 through 6 there is shown second body 16 which contains two main elements a fixed housing 40 and a rotating housing 42. As indicated above, hollow shaft 70 of rotating arm 14 has a square or polygonal outer circumference and bore 59 has a square cross-section for receiving preferably square shaft 29. Shaft 70 in turn engages a bushing 62 of housing 40 which has a square internal bore 41 for receiving hollow shaft 70. Bushing 62 is integral with fixed housing 40. Thus, bushing 62 of fixed housing 40 non-rotatably couples the housing 40 to shaft 70. Moveable housing 42 contains a cylindrical bushing 46 rotatably mounted on bushing 62 Bushing 46 is rotatably mounted on bushing 62 and thus with respect to shaft 70 so that housing 42 can rotate with respect to fixed housing 40. In turn, rotating housing 42 is coupled to rod 102 and thus as housing 42 rotates shaft 102, 104 and cutting guide 100 are rotated in the varus-valgus direction with respect to the tibia. Shaft 102 is coupled to rotating bushing 46 by a coupling member 60 preferably made integral with housing 42. Shaft 102 may be coupled within coupling member 60 such as by threading rod 102 therein or by welding an end of shaft 102 into the coupling element 60. Optionally, the entire assembly of shaft 70, arm 14 and block 12 can be slid in direction "A" through bushing 62 to space the rod 102 closer or further from the long bone. The position of the entire assembly is locked by spring detent 160.

Figure 6:
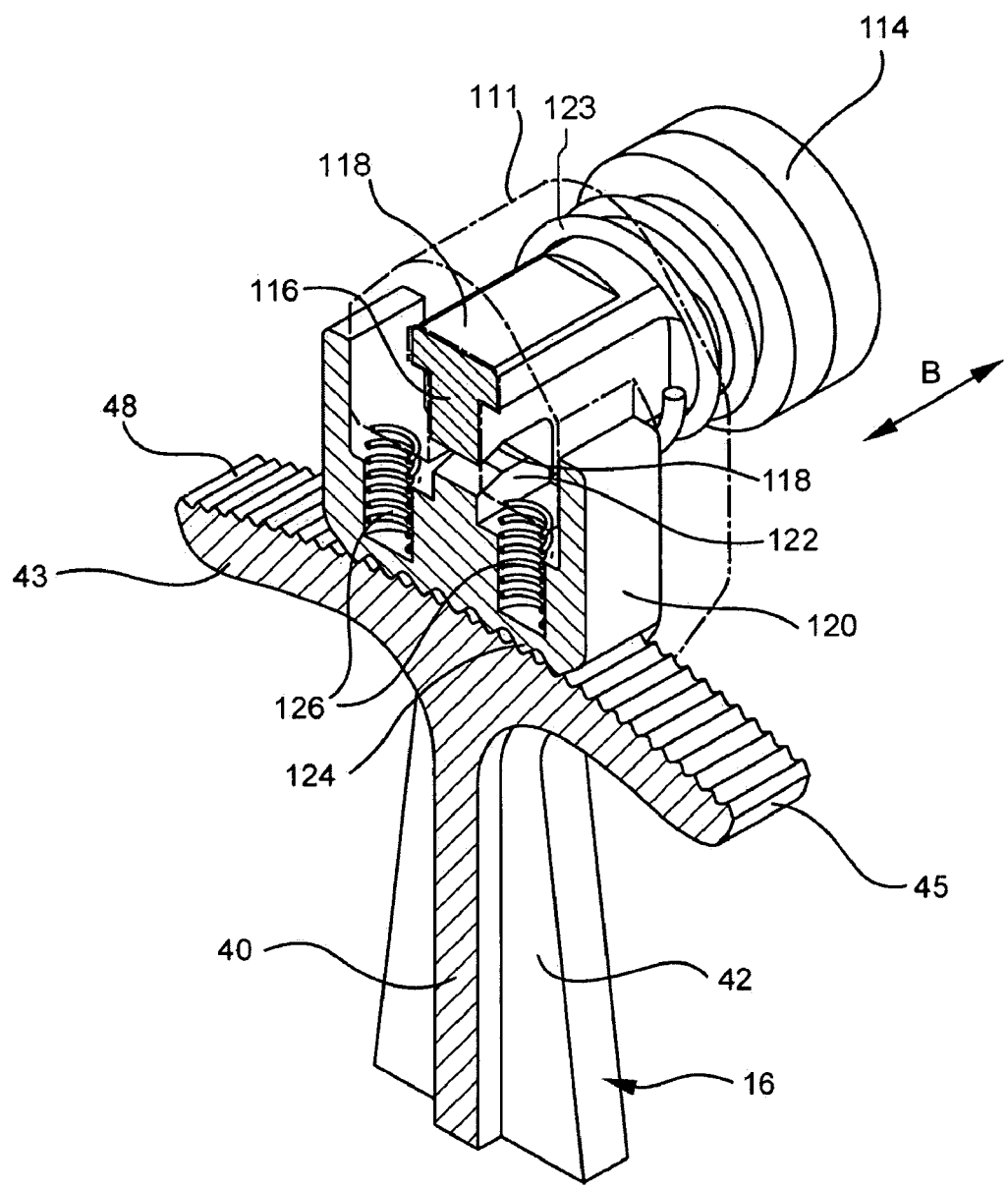
FIG. 6 is an enlarged view of the varus-valgus adjustment mechanism of FIGS. 1 and 4.

In the preferred embodiment, as best seen in FIG. 6, fixed housing 40 includes an arm 43 having a flanged portion 45 at a free end thereof covered with teeth 48. The teeth 48 of flanged portion 45 are preferably located at 1 degree increments with respect to the central axis of the fixed housing 40.

As shown in FIGS. 4 and 6, the end 111 of housing 42 supports a button 114 which has a ramped shaft portion 116. Shaft 116 has a ramp surface portion 118 which functions in a similar manner as ramp 32 of shaft 29 described above. A spring-loaded shuttle 120 having a ramp portion 122 engageable with ramp portion 118 of shaft 116 is mounted on the tooth surface 48 of flange 43. Shuttle 120 includes teeth 124 which are spring-biased into contact with teeth 48 by a spring 126. Button 114 is spring biased in a direction opposite of direction "B" shown in FIG. 6 by spring 123 so that the engagement of ramps 118 and 122 cause shuttle 120 to lock the system. Thus, the structure is basically the same as described above for shuttle 26 and shaft 29.

In use, movement of button 114 and consequently shaft 116 in a direction "B" shown on FIG. 6 releases the spring-loaded shuttle 120 to allow rotational movement of housing 42 of second rotating body 16 about bushing 62 to adjust the varus-valgus angle of cutting block 100. When pressure on button 114 is released, spring 123 causes ramps 118 and 122 to engage forcing teeth 124 of shuttle 120 into engagement with teeth 48 of flange portion 43.

During use, movement in the varus-valgus (arrows "C" in FIG. 3) direction is generally plus or minus 6 degrees and movement in the flexion-extension (arrows "D" of FIG. 2) direction is generally from zero to plus five degrees from the position wherein planes containing the axis of shaft 102 and shaft 40 are orthogonal.

The preferred method of use of the instrument for the tibia will now be described. Initially, the surgeon inserts rod 13 into the medullary canal of the tibia with the upper or proximal portion of the rod extending beyond the tibial plateau. The surgeon then mounts the locking intramedullary tibial jig 10 on rod 13 via bores 18 of anchoring block 12. Anchoring block 12 is slid distally on rod 13 to contact the top of the tibia. The general proximal-distal location of instrument 10 on rod 13, and consequently cutting block 100, can be set by the proper positioning of anchoring block 12 on rod 13. The surgeon then fine tunes the level of the proximal-distal cut by the use of wheel 108 to adjust the proximal-distal location of cutting block 100. The surgeon then sets the flexion-extension angle and then sets the varus-valgus angle using the intramedullary alignment system. The alignment can be checked with an external alignment rod coupled to bore 132. The location in rotation can be fixed by a pin extending through bore 130 of block 12. To adjust or re-adjust, the angular positions, all the surgeon must do is depress either button 34 or button 114, make the adjustments in direction "C" or "D" and then release the button to lock the jig at the desired flexion-extension and varus-valgus angle. As discussed above, the angle adjustment of the locking rachet pawl is in one degree increments, although finer or coarser increments would be possible. After cutting block 100 is properly positioned, it is pinned to the proximal tibia in a known manner. The alignment jig 10 is then removed from cutting block 100 and the proximal tibial cut is made. While use of instrument 10 has been described for use on the tibia or on a femur for the distal cut is also contemplated.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A locking intramedullary jig for use in bone resection comprising:
   an axially extending intramedullary rod for insertion into the medullary canal of a bone;
   a slide block mounted on said rod for movement along an axis of said rod in the axial direction, said slide block having a pivot point at one end thereof and a tooth portion at a second end thereof;

a first rotating body pivotally coupled to said pivot point on said slide block for rotation about a first axis, said rotating body including a toothed locking member moveably mounted thereon, said toothed locking member including a toothed locking spring element biasing said toothed locking member into releasable locking engagement with said toothed portion of said slide block; and a bone resection guide coupled to said first rotating body;

said first rotating body further including a spring biased shaft mounted thereon with a first end engageable with said toothed locking member thereon for moving said toothed locking member relative to said first rotating body against the toothed locking spring element into locking engagement with said toothed portion of said slide block.

2. The locking jig for use in bone resection as set forth in claim 1 wherein said spring biased shaft is moveable against said spring to a position which allows movement of teeth on said toothed locking member away from teeth on said slide block toothed portion to permit relative movement therebetween.

3. The locking jig for use in bone resection as set forth in claim 1 further comprising a second body having a rotating body part rotatably coupled to said first rotating body and a non-rotatable part, said second body having said bone resection guide mounted thereon.

4. The locking jig for use in bone resection as set forth in claim 3 wherein said second body has a non-rotatable toothed portion mounted on said non-rotatable part, said rotatable portion coupled to said bone resection guide, said rotatable portion of said second body having a locking pawl with a toothed portion for releasable locking engagement with said non-rotatable toothed portion of said second body.

5. The locking jig for use in bone resection as set forth in claim 4 wherein said first end of said spring biased shaft is engageable with said toothed locking pawl on said rotatable part for moving said toothed locking pawl into engagement with said non-rotatable toothed portion.

6. The locking jig for use in bone resection as set forth in claim 5 wherein said spring biased shaft is moveable against the spring to a position which allows movement of teeth on said toothed locking pawl away from the teeth on said non-rotatable toothed portion.

7. The locking jig as set forth in claim 3 wherein said bone resection guide is mounted on said second body for movement in a direction parallel to said intramedullary rod axis.

8. The locking intramedullary jig for use in bone resection as set forth in claim 1, wherein when said rotating body is released from locking engagement with said toothed portion of said slide block, said shaft is capable of moving along at least a portion of a second axis perpendicular to said axis of said rod.

9. The locking intramedullary jig for use in bone resection as set forth in claim 1, wherein said second axis lies in a plane parallel to said axis of said rod.

10. The locking jig for use in bone resection as set forth in claim 1, wherein at least a portion of said toothed portion is positioned on said sliding block along at least a portion of a second axis that is perpendicular to said axis of said rod.

11. The locking jig for use in bone resection as set forth in claim 1, wherein at least a portion of said toothed portion extends along a sloped angle.

12. The locking jig for use in bone resection as set forth in claim 11, wherein an angle of said sloped angle increases in a direction away from said intramedullary rod.

13. An alignment system for use in setting the angular position of a bone cutting block with respect to a bone surface to be resected comprising:

a bone contacting element extending along a first axis;

a first body mounted on said bone contacting element having a first portion non-rotatably coupled to said element and a second portion pivotally coupled to said first portion for rotation about a second axis perpendicular to said first axis, said second portion having a shaft extending therefrom, said first portion having a toothed portion and said second portion having a moveable toothed locking member mounted thereon, said locking member spring-biased into engagement with the toothed portion of said first portion, said second portion including an actuation element mounted in a bore in said shaft for moving said locking element against said spring out of engagement with said first portion toothed portion;

a second body having a first and second portions, the first portion of said second body non-rotatably coupled to the first body second portion and the second portion of said second body portion rotatably coupled to said shaft of said first body second portion, said first portion of said second body having a toothed portion and said second body second portion having a toothed locking member moveably mounted thereon said locking member spring-biased into engagement with the toothed portion of said second body first portion, said second body second portion including an actuation element for moving said locking element against said spring out of engagement with said first member toothed portion; and a bone cutting block mounted on said second body second portion.

14. The locking system as set forth in claim 13 wherein said second portion of said second body is rotatably coupled to said first body second portion for rotation about a third axis perpendicular to said first and second axis.

15. The locking system as set forth in claim 14 wherein said bone contacting element is a rod for insertion into the intramedullary canal of a long bone.

16. The locking system as set forth in claim 15 wherein said long bone is a tibia and rotation of said first body about said second axis moves the cutting block in the flexion-extension direction and rotation of said second body about said third axis moves the cutting block in the varus-valgus direction.

17. An alignment system for use in setting the angular position of a bone cutting block with respect to a bone surface to be resected comprising:

a first element capable of being coupled to the bone;

a second element rotatably coupled to said first element for rotation about a first axis;

a third element having the cutting block mounted thereon rotatably coupled to said second element for rotation about a second axis generally perpendicular to said first axis and lying in a plane parallel to said first axis;

a first rachet mechanism having a curved surface including a plurality of teeth mounted therein, the rachet mechanism coupled to said first and second elements for locking the rotational position of said second element with respect to the first element;

a second rachet mechanism for locking the rotational position of said third element with respect to the second element;

wherein said first element is coupled to an intramedullar rod;

wherein said second element is rotatable about a medially-laterally extending axis;

wherein said third element is rotatable about an anterior-posterior extending axis;

wherein the first rachet mechanism includes a first spring biased locking pawl mounted between said first and second elements for selectively locking the rotational position of said first and second elements about said medial-lateral axis and said second rachet mechanism includes a second spring biased locking pawl mounted on said third element for locking the rotational position of said second and third elements about said anterior-posterior axis.

18. The alignment system as set forth in claim 17 wherein the first and second locking pawls are spring biased towards the locked position.

19. The alignment system as set forth in claim 17 wherein the first element is mounted on the intramedullary rod in the proximal-distal direction.

20. The alignment system as set forth in claim 19 wherein said cutting block is mounted on said third element for movement in the proximal-distal direction.

21. The alignment system as set forth in claim 17 wherein the first locking pawl has teeth engageable with teeth on the one of the first and second elements and wherein the second locking pawl has teeth engageable with teeth of one of the second or the third element.

22. The alignment system as set forth in claim 21 wherein the teeth on the first and second locking pawls are spaced in 1° increments about said medial-lateral axis and said anterior-posterior axis.

23. The alignment system as set forth in claim 21 wherein said spring has a force sufficient to keep the teeth in constant engagement but which force allows the teeth to disengage on relative movement between the first and second elements and said second and third elements.

* * * * *

UNITED STATES PATENT AND TRADEMARK OFFICE
CERTIFICATE OF CORRECTION

PATENT NO. : 7,618,420 B2
APPLICATION NO. : 11/060154
DATED : November 17, 2009
INVENTOR(S) : Carlos E. Collazo It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 678 days.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,618,420 B2
APPLICATION NO. : 11/060154
DATED : November 17, 2009
INVENTOR(S) : Carlos E. Collazo It is certified that error appears in the above-identified patent and that said Letters Patent is hereby corrected as shown below:

On the face page of the patent, Col. 2, Abstract, Line 2, insert --,-- after "tibial"

On the face page of the patent, Col. 2, Abstract, Line 12, insert --of-- before "the anchoring block"

Col. 1, Line 27, insert --,-- after "slippery gloves"

Col. 1, Line 49, insert --of-- after "degrees"

Col. 3, Line 11, replace "a" after mounted on with --an--

Col. 3, Line 39, insert --,-- after "indirectly"

Col. 4, Line 58, replace "Direction" with --direction--

Col. 5, Line 17, insert --a-- after "about"

Col. 5, Line 25, insert --the-- after "about"

Col. 5, Line 31, insert --,-- after "elements"

Col. 5, Line 41, insert --.-- after "62"

Col. 6, Line 38, delete "," after "re-adjust"

Col. 8, Line 18, insert --a-- after "second body having"

Col. 8, Line 36, replace "axis" with --axels--

Col. 8, Line 64, replace "intramedullar" with --intramedullary--

Col. 10, Line 5, delete "the" after "with teeth on"

Signed and Sealed this

Fourteenth Day of December, 2010

David J. Kappos
*Director of the United States Patent and Trademark Office*